United States Patent
Bernat et al.

(10) Patent No.: US 9,404,892 B2
(45) Date of Patent: Aug. 2, 2016

(54) GAS CONCENTRATION SENSOR, MOTOR VEHICLE HAVING A GAS CONCENTRATION SENSOR, AND METHOD FOR MEASURING GAS CONCENTRATION

(75) Inventors: Tobias Bernat, Regensburg (DE); Armin Hollstein, Regensburg (DE)

(73) Assignee: Continental Automotive GmbH, Hannover (DE)

( * ) Notice: Subject to any disclaimer, the term of this patent is extended or adjusted under 35 U.S.C. 154(b) by 1001 days.

(21) Appl. No.: 13/576,644

(22) PCT Filed: Feb. 1, 2011

(86) PCT No.: PCT/EP2011/051359
§ 371 (c)(1),
(2), (4) Date: Oct. 5, 2012

(87) PCT Pub. No.: WO2011/095470
PCT Pub. Date: Aug. 11, 2011

(65) Prior Publication Data
US 2013/0199265 A1  Aug. 8, 2013

(30) Foreign Application Priority Data
Feb. 2, 2010  (DE) .......................... 10 2010 006 576

(51) Int. Cl.
*G01N 29/36* (2006.01)
*G01N 29/42* (2006.01)
(Continued)

(52) U.S. Cl.
CPC ........... *G01N 29/036* (2013.01); *G01M 15/102* (2013.01); *G01N 29/02* (2013.01); *G01N 2291/012* (2013.01);
(Continued)

(58) Field of Classification Search
CPC ............ G01N 2291/102; G01N 29/02; G01N 29/036; G01N 2291/012; G01N 2291/0212; G01N 2291/0217; G01M 15/102
See application file for complete search history.

(56) References Cited

U.S. PATENT DOCUMENTS 2,865,196 A  12/1958 Bordenave et al.
4,119,950 A  10/1978 Redding
(Continued)

FOREIGN PATENT DOCUMENTS

| DE | 360 10 85 A1 | 7/1987 |
|---|---|---|
| DE | 690 17 376 T2 | 6/1995 |
| DE | 198 41 154 A1 | 4/2000 |

OTHER PUBLICATIONS

Habaguchi, Masayuki, et al. "Gasoline Vapor Concentration Sensor-On Board Measurement by Ultrasonic Pulse." JSAE Review 17.1 (1996): 92-92.*
English Translation of Habaguchi, Masayuki, et al. "Gasoline Vapor Concentration Sensor-On Board Measurement by Ultrasonic Pulse." JSAE Review 17.1 (1996) pp. 1-12.*
Sultan, Myrna C., et al. Closed loop canister purge control system. No. 980206. SAE Technical Paper, 1998.*
(Continued)

*Primary Examiner* — Lisa Caputo
*Assistant Examiner* — Punam Roy
(74) *Attorney, Agent, or Firm* — Cozen O'Connor

(57) ABSTRACT

A motor vehicle having a gas concentration sensor and a method for measuring gas concentration using the gas concentration sensor the gas concentration sensor having a sound transmitter, a sound receiver and a control device by which a phase shift between the sound signal transmitted by the sound transmitter and a sound signal received by the sound receiver can be controlled to a predefinable phase shift. A change in a composition of a gas mixture can be detected by an analysis unit on the basis of a change in frequency of the sound signal relative to a frequency of a reference sound signal.

15 Claims, 2 Drawing Sheets

(51) Int. Cl.
*G01N 29/036* (2006.01)
*G01M 15/10* (2006.01)
*G01N 29/02* (2006.01)

(52) U.S. Cl.
CPC ............ *G01N 2291/0212* (2013.01); *G01N 2291/0217* (2013.01); *G01N 2291/102* (2013.01)

(56) References Cited

U.S. PATENT DOCUMENTS

| | | | |
|---|---|---|---|
| 4,255,964 A * | 3/1981 | Morison | 73/24.01 |
| 4,275,363 A * | 6/1981 | Mishiro | B06B 1/0253 |
| | | | 310/316.01 |
| 5,060,514 A | 10/1991 | Aylsworth | |
| 5,313,820 A | 5/1994 | Aylsworth | |
| 5,467,637 A | 11/1995 | Hasegawa et al. | |
| 6,308,572 B1 * | 10/2001 | Ishikawa | G01N 29/024 |
| | | | 73/24.01 |
| 6,418,782 B1 | 7/2002 | Sato et al. | |
| 2002/0017124 A1 * | 2/2002 | Dempster | G01N 29/024 |
| | | | 73/23.2 |
| 2002/0115198 A1 * | 8/2002 | Nerenberg et al. | 435/287.2 |
| 2004/0129056 A1 * | 7/2004 | Hok et al. | 73/24.06 |
| 2005/0034536 A1 * | 2/2005 | Kondo | 73/861.27 |

OTHER PUBLICATIONS

J. S. Olfert, M. D. Checkel, C. R. Koch; Acoustic method for measuring the sound speed of gases over small path lengths; Database accession No. E200724106496841; Review of Scientifics Instruments 2007; American Institute of Physics; in vol. 78, No. 5; 2007; US; XP002643985.

J. T. Tinge; K. Mencke; L. Bosgra and A. A. H. Drinkenburg; "Ultrasonic gas analyser for high resolution dtermination of binary-gas composition"; Hournal of Physics. E. Scientific Instruments, Nov. 1, 1986; IOP Publishing, Bristol, GB,; in vol. 19, No. 11, pp. 953-956; XP020017718; ISSN: 0022-3735.

* cited by examiner

GAS CONCENTRATION SENSOR, MOTOR VEHICLE HAVING A GAS CONCENTRATION SENSOR, AND METHOD FOR MEASURING GAS CONCENTRATION

CROSS REFERENCE TO RELATED APPLICATIONS

This is a U.S. national stage of application No. PCT/EP2011/051359, filed on 1 Feb. 2011. Priority is claimed on German Application No. 10 2010 006 576.5 filed 2 Feb. 2010, the content of which is incorporated here by reference.

BACKGROUND OF THE INVENTION

1. Field of the Invention

The present invention relates to a gas concentration sensor, to a motor vehicle having a gas concentration sensor, and to a method for measuring gas concentration.

2. Description of the Prior Art

Tightening of the emission control regulations in the European Union and in the USA has led to requirements that emission limiting values are not exceeded during a cold start of an internal combustion engine. In these cold start phases, a filter for filtering fuel vapors is frequently scavenged with fresh air. For example, the filter is an activated carbon filter by which fuel vapors are prevented from escaping from a tank system into the environment. The air provided with a proportion of fuel is fed into an intake section of the internal combustion engine from the activated carbon filter. A proportion of fuel is therefore introduced into a fuel/air mixture of the internal combustion engine by the air from the activated carbon filter.

However, during the cold start phase of the internal combustion engine, a lambda sensor arranged in an exhaust system of the internal combustion engine is usually not yet in an operationally ready state. For this reason, the exhaust gas emissions cannot be reduced to a minimum by a control device of the motor vehicle owing to measured values detected with the lambda sensor. For this reason it is appropriate to determine a proportion of fuel in the air leaving the activated carbon filter.

To determine a composition of a gas mixture, acoustic measuring methods are known that make use of the fact that the speed of sound in gas mixtures depends on the composition of the gas mixture. This effect may be used to measure the mixture ratio of two gases whose substances are known. For example, the speed of sound in 100% air at a temperature 0° C. is 331.6 m/s. This exemplary speed of sound is reduced to approximately 225 m/s when propane is mixed and if only propane is then present. The known acoustic measuring methods usually operate in the ultrasonic range. Furthermore, the speed of sound in a gas or gas mixture is influenced by temperature and pressure of the gas or gas mixture. However, the pressure and temperature are computationally related so that given knowledge of the pressure or temperature the respective other variable can be determined.

A known acoustic measuring method operates in a way analogous to an echo sounder. In this context, a wave packet of defined frequency and length is transmitted into a measuring chamber from a sound generator to a receiver at a defined distance. The receiver is usually arranged on a side of the measuring chamber lying opposite the sound generator, at a same height as the sound generator. A transit time between the emission of the wave packet and the arrival at the receiver is measured. The mixture ratio of the gases present in the measuring chamber is determined from this transit time.

Frequencies in a range from 100 to 400 kHz are used for the "echo sounding" method. In this frequency range, a narrow frequency lobe is formed at the transmitter and, therefore only a small number of scattered signals are formed. Furthermore, the scattered signals travel larger distances than the measurement signal, as a result of which the influence of the scattered signals on the measurement signal is reduced because amplitude attenuation is higher the higher the frequency used.

A disadvantage of the above "echo sounding" method is that the transducers used are very expensive compared to simple piezo-flexural vibrators or electrodynamic transducers, and that the technical complexity of the measurement is correspondingly greater.

A further known acoustic measuring method is a phase measuring method. This likewise operates with a measuring chamber in which a sound generator and a receiver are located at a defined distance. A change in the speed of sound brought about by the composition of the gas mixture passed through is determined from a phase shift between a transmission signal of the sound generator and a reception signal of the receiver. Owing to the change in the speed of sound, a mixture ratio of the gases in the measuring chamber can be determined.

A disadvantage of this method is that the measuring range is restricted to a maximum phase shift of one wavelength. If, for example, a phase shift of 380° were to occur, this would not be detected by the phase measuring method. In this example, a phase shift of 20° would be detected with the phase measuring method.

Therefore, this phase measuring method also requires large wavelengths, that is to say low frequencies, to detect large changes in transit time. However, the lower the frequency being used, the greater the effects of scattered signals. These scattered signals are reflected at the measuring chamber walls and interfere with the measurement signal along the measured section and leads to further phase shifts. Furthermore a signal amplitude of the measuring signal is reduced to unmeasurable values. For this reason, either a voluminous measuring chamber or special attenuating elements are used to minimize the influence of scattered signals.

An acoustic measuring method which is also known is based on a change in a resonant frequency of a quartz oscillator on the basis of an accumulation of gas molecules. The accumulation of gas molecules at the quartz oscillator brings about an increase in the mass of the quartz oscillator, which in turn results in a change in the resonant frequency of the quartz oscillator.

Other approaches to determine a gas composition operate with optical methods. These optical methods are, however, unsuitable in the field of motor vehicles owing to their susceptibility to soiling. Alternatively, methods are known which operate using heated ceramics, which for safety reasons, are not able to be used in the field of the fuel supply in a motor vehicle in particular in view of the risk of explosion.

SUMMARY OF THE INVENTION

An object of one embodiment of the present invention is to make available a gas concentration sensor that does not have the disadvantages of the methods presented above and can be used in a motor vehicle, as well as to provide a corresponding method for measuring gas concentration.

A gas concentration sensor according to one embodiment of the invention comprises a sound transmitter, which emits a sound signal, a sound receiver that receives the sound signal emitted by the sound transmitter, and a control device by with which a phase shift between the sound signal emitted by the sound transmitter and the sound signal received by the sound receiver can be adjusted a predefinable phase shift, wherein a change in a composition of a gas mixture can be determined by an evaluation unit based on a change in frequency of the sound signal relative to a frequency of a reference sound signal.

The gas concentration sensor according to one embodiment of the invention has a sound transmitter, a sound receiver and a control device. The sound transmitter emits a sound signal while the sound receiver receives the emitted sound signal. A distance between the sound transmitter and the sound receiver is, in particular, a multiple of ¼ of the wavelength of the reference sound signal.

With the control device it is possible to adjust a phase shift between the sound signal emitted by the sound transmitter and the sound signal received by the sound receiver to a predefinable phase shift. In particular, the predefinable phase shift is defined once. During the later operation of the gas concentration sensor, the control device automatically ensures that the phase shift that has been predefined once is maintained. Alternatively, the predefinable phase shift can be changed at the start of each measurement.

An evaluation unit determines a change in a composition of a gas mixture based on a change in frequency of the sound signal relative to a frequency of a reference sound signal. For example, this is a gas mixture of two gases. The reference sound signal relates in this case to one of the two gases present for the reference measurement with a proportion of 100%.

An initial consideration with the gas concentration sensor according to one embodiment of the invention is that a measuring capability reduced by scattered signals in the phase shift measuring method described above depends on several factors. These factors are a geometry of the measuring chamber used, attenuation of the scattered signals by a gas or gas mixture in the measuring chamber, and a frequency of the measuring signal. The geometry of the measuring chamber is equivalent to a distance that the scattered signals have to travel.

In the case of a change in concentration in an exemplary gas mixture, the phase shift between the measuring signal emitted by the sound transmitter and the sound signal received by the sound receiver changes. Furthermore, the amplitude of the measuring signal changes. An objective of the gas concentration sensor according to one embodiment of the invention is to compensate for these changes in phase shift and amplitude. For this purpose, a suitable frequency control by a control device is proposed.

A change in frequency of the measuring signal acts on the scattered signals in the same way, which in turn results in constant interference conditions. In particular, the amplitude of the measuring signal and a phase shift between the emitted sound signal and the received sound signal caused by the scattered signals remain constant. Compared to the phase measuring method, the present concentration sensor according to one embodiment of the invention therefore uses a phase-dependent change in frequency instead of the phase shift as its measurement variable.

An advantage of the present gas concentration sensor is that a large-volume measuring chamber, as is necessary in the prior art, is no longer necessary. This is due to the fact that with the present gas concentration sensor it is no longer necessary for scattered signals to "peter out". For this reason, the gas concentration sensor can have a shorter distance between the sound transmitter and the sound receiver compared to the prior art. Furthermore, the sensor can operate with a frequency that is higher compared to the prior art. An influence of scattered signals on the measuring signal is also minimized.

In one particularly advantageous embodiment, the sound signal of the sensor is in the audible sound range up to the ultrasonic range. The term audible sound range comprises, in particular, a sound range which can be perceived acoustically by a person.

It is also advantageous if the sound transmitter and the sound receiver are piezo-transducers or dynamic transducers. Both types of transducers are cost-effective transducers, with the result that they are suitable for use in the field of motor vehicles. Alternatively, Sell transducers can be used as sound transmitters and sound receivers.

It is particularly preferred that the sensor comprises a measuring chamber equipped with sound-absorbing surfaces in its interior. In this way, the precision of the sensor can be increased further. In addition, a definable environment, for example a definable temperature, can be set within the measuring chamber.

It is also advantageous if the predefinable phase shift is 0°. It is also preferred if the frequency of the reference sound signal relates to 100% air. In particular, a component of foreign gases in the air can thus be detected. When the gas concentration sensor is used in a motor vehicle, the foreign gases are fuel vapors.

It is also preferred that the control device of the sensor is a PLL (Phase Locked Loop) circuit. Using the PLL circuit it is possible to implement the control of the frequency of the emitted sound signal easily and inexpensively. In the PLL circuit, the frequency of the emitted sound signal is adjusted by a phase comparator to a predefinable phase shift with respect to the reception signal.

The emitted sound signal is generated by a voltage-controlled oscillator (VCO). The phase shift is preferably 0°.

The phase comparator operates as a three-point controller and does not measure the phase shift in terms of magnitude. The phase comparator compares the emitted sound signal and the received sound signal as to whether the frequency of the emitted sound signal has to increase, decrease, or remain constant for the phase shift to correspond to the predefinable phase shift.

Furthermore the PLL circuit has a latching range. Latching range means that the PLL circuit can control only within a specific frequency range, the latching range. This latching range is selected in accordance with a measuring range of the gas concentration sensor. For this reason in the case of the mixture of two gases the selection of the wavelength and therefore of the frequency of the reference sound signal is carried out in such a way that an anticipated range of change in the composition of the gases corresponds at maximum to one signal period of the reference sound signal. This ensures that the PLL circuit operates in a stable control range. For example, a frequency X is used for a first gas. This frequency X is the reference frequency. If a second gas is then added, the signal period of the reference signal X can change at most by one signal period, that is to say at maximum by a phase shift of 360°.

One advantage of the PLL circuit is that extraneous frequencies, which can occur when the gas concentration sensor is used in a motor vehicle, remain largely without effect. The extraneous frequencies are, for example, vehicle frequencies transmitted by solid-borne sound into a measuring chamber of the gas concentration sensor.

In addition to the PLL circuit, the sensor can also have a boosting circuit that comprises a Schmitt trigger. The Schmitt trigger generates digital square-wave signals that are necessary for the phase comparator.

Furthermore, the gas concentration sensor can have a temperature sensor. With the temperature sensor it is possible to detect a temperature, in the measuring chamber. By the temperature sensor it is therefore possible to implement a further improvement in the measuring accuracy of the gas concentration sensor. This applies, in particular, when the sensor is connected to a control device or an evaluation unit in which a correlation of the speed of sound and the temperature for a plurality of gases is stored.

A motor vehicle has a gas concentration sensor according to one embodiment of the invention on a line of the motor vehicle. In this way, gas concentrations in lines of the motor vehicle can be detected.

The gas concentration sensor according to one embodiment of the invention is advantageously arranged between a filter device for filtering fuel vapors and an internal combustion engine and can be connected to a control unit of the motor vehicle. The filter device is an activated carbon filter that absorbs fuel vapors emerging from a tank of the motor vehicle. The gas concentration sensor detects, during a scavenging process of the activated carbon filter, the proportion of fuel vapor, emerging from the activated carbon filter, in the scavenging air.

It is therefore particularly preferred that the gas concentration sensor can determine a change in a proportion of fuel vapor in the gas mixture.

A method for measuring a gas concentration, which uses a gas concentration sensor according to one embodiment the invention, has the following steps: emitting a sound signal with a sound transmitter, receiving of the emitted sound signal with a sound receiver, adjusting a phase shift between the emitted sound signal and the received sound signal to a predefinable phase shift by a control device, and determining a change in a composition of a gas mixture on the basis of change in frequency of the sound signal by an evaluation unit.

The present method for measuring gas concentration has all the advantages of the gas concentration sensor described above. With respect to the sequence of the method, reference is made to the description of the gas concentration sensor and the method of functioning thereof.

The gas concentration sensor is advantageously arranged in a motor vehicle between a filter device for filtering fuel vapors and an internal combustion engine wherein the method for measuring gas concentration has the further step transmitting the determined change in the composition of the gas mixture to a control unit of the motor vehicle. In this way, a proportion of fuel, which is fed to the internal combustion engine, can be detected in scavenging air of the filter. The control unit of the motor vehicle can then correspondingly adapt the fed-in quantity of fuel so that the combustion behavior of the internal combustion engine is not worsened.

According to one preferred embodiment, a maximum measuring range of the sensor is divided into three or five regions, and a signal which corresponds to the respective region is transmitted to the control unit as an indication of a change in the composition of the gas mixture. In this way, discrete measurement of the concentration of the fuel vapor in the scavenging air is not necessary. All that occurs is merely a classification as to whether the concentration is in a low, medium, or high range. On the basis of this information, the control unit can adapt the quantity of fuel, which is fed to the internal combustion engine.

The method for measuring gas concentration is carried out, in particular, in a motor vehicle at a time that a lambda probe of the motor vehicle is in a non-operationally ready state. This occurs, in particular, directly after a cold start of an internal combustion engine of the vehicle. In this way, compliance with predefined emission values for the internal combustion engine can be implemented even during a warming up phase of the internal combustion engine.

The method for measuring gas concentration having the further steps is also advantageous: detecting a temperature and taking into account the detected temperature in the determination of the change in the composition of the gas mixture. Since the properties of gases change, in particular as a function of the temperature, the accuracy of the measuring method is improved by detecting and taking into account the temperature.

BRIEF DESCRIPTION OF THE DRAWINGS

In the text which follows, the present invention will be described in detail by means of an embodiment and with reference to the accompanying drawings, in which.

DETAILED DESCRIPTION OF THE PREFERRED EMBODIMENTS

The gas concentration sensor according to one embodiment of the invention is arranged in a line of a motor vehicle. In particular, the line is a line between an activated carbon filter and an air feed line of an internal combustion engine of the vehicle.

Figure 1:
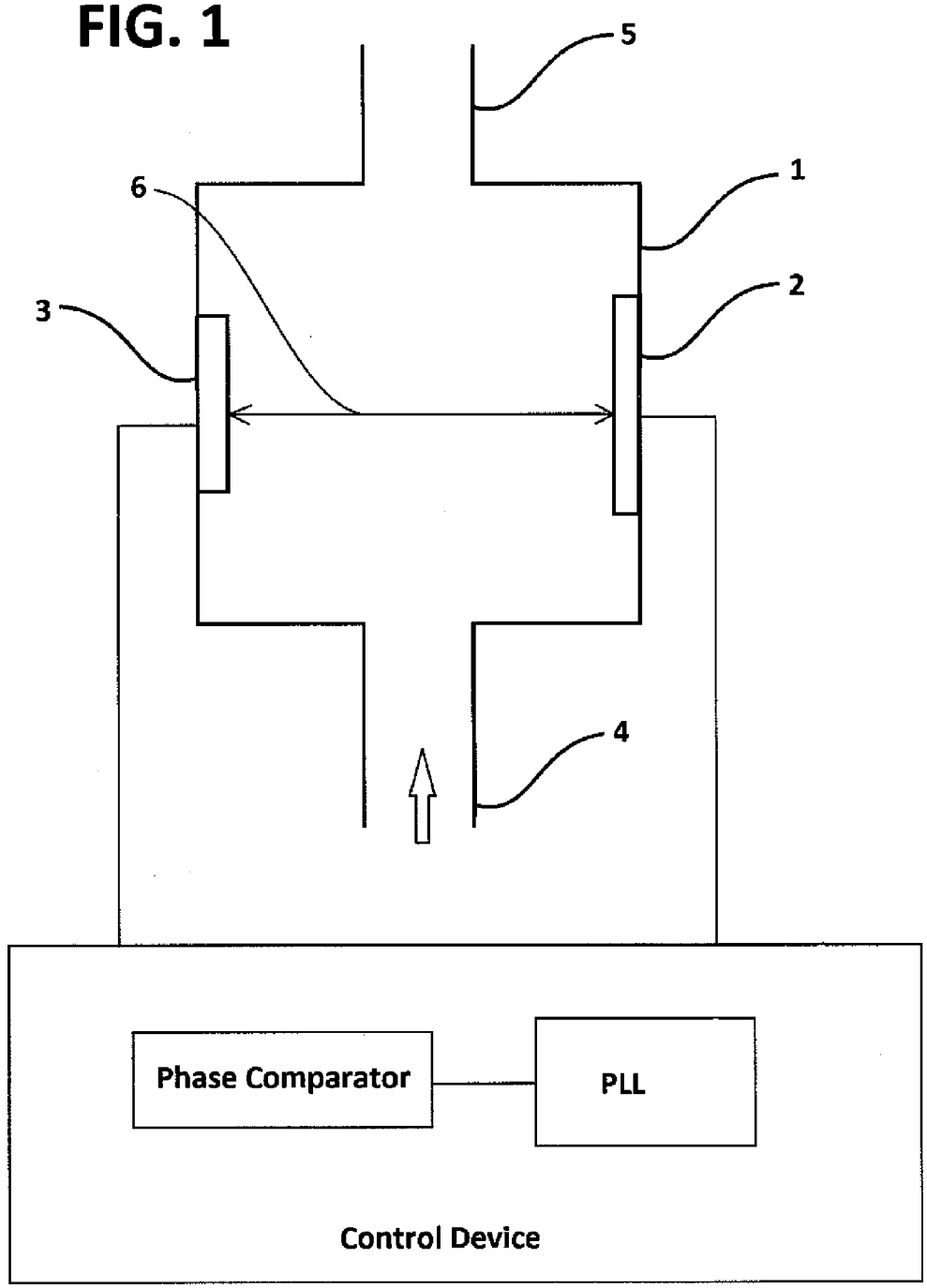
FIG. 1 is a schematic illustration of a gas concentration sensor according to the present invention.

According to FIG. 1, the gas concentration sensor includes a sound transmitter 3 and a sound receiver 2. A measuring section is formed between the sound transmitter and the sound receiver 2. The sound transmitter 3 and the sound receiver 2 are, in particular, piezo-transducers or dynamic transducers. The sound signal used is, in particular, in the audible sound range up to the ultrasonic range.

Furthermore, the gas concentration sensor has a measuring chamber 1 with a gas inlet opening 4 and a gas outlet opening 5. However, the ultrasonic transmitter 3 and the sound receiver 2 can be arranged directly in a line of the motor vehicle, without a measuring chamber. For example, the sound transmitter and the sound receiver 2 can be embodied as an integral component of the line.

An exemplary distance between the sound transmitter 3 and the sound receiver 2 is 51 mm, wherein a frequency of 4.111 kHz is used. This distance applies, in particular, when 100% air is used as a gas for determining a reference sound signal at a temperature of 25° C. The distance between the sound transmitter 3 and the sound receiver 2 should generally be a multiple of ¼ wavelength of the frequency used, wherein in addition a delay owing to the control circuit used has to be taken into account. Therefore, as a rule of thumb, usually a distance of ⅝ of the wavelength used is applied to the distance between the sound transmitter and the sound receiver. Furthermore, signal inversion is necessary with this distance since ⅘ of the wavelength correspond to a phase shift of 180°.

Figure 2:
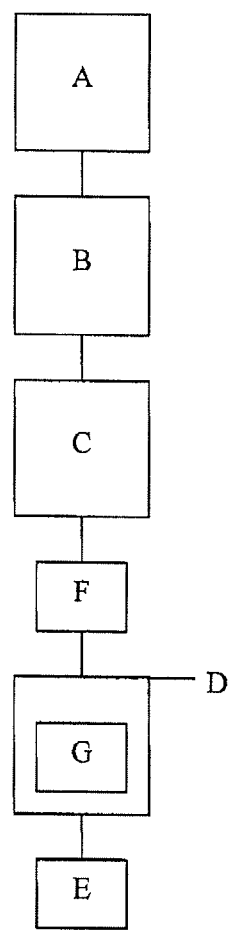
FIG. 2 is a flowchart of a method for measuring a gas concentration.

The method according to one embodiment of the invention will now be explained with reference to FIG. 2. In a step A, the sound transmitter 3 emits a sound signal. This sound signal is received by the sound receiver 2 in a step B. As an alternative to the embodiment illustrated in FIG. 1, the sound transmitter 3 and sound receiver 2 can also be arranged on a same side. However, with this design a reflector is always necessary at the location at which the sound receiver 2 is arranged in FIG. 1. In this way, a propagation distance for the sound signal can be doubled with the same size of the measuring chamber.

Alternatively, the receiver as a separate component can be dispensed with if the sound generator is also operated as a receiver. A reflection surface, which reflects the sound signal emitted by the sound generator, is used at the position of the original receiver. In this case, the sound generator has to be switched over in time to a reception mode. In time means that switching over of the sound generator has to take place before the earliest possible time of arrival of the sound signal at the location of the sound generator.

As already explained, the region between the sound transmitter 3 and the sound receiver 2 is firstly filled with a gas with 100% concentration. This signal is used as a reference sound signal and, for example, a phase shift of 0° is set. If the gas composition in the region between the sound transmitter 3 and the sound receiver 2 then changes, a phase shift occurs. This phase shift is compensated for by the control device since the control device maintains the predefinable phase shift. The control device is, in particular, a PLL (Phased Locked Loop) circuit. In this circuit, a phase comparator adjusts the frequency of the transmission signal to a predefinable phase shift with respect to the reception signal. The phase comparator operates as a three-point controller and therefore does not measure the phase shift quantitatively but merely detects whether a frequency of an internal VCO (Voltage Controlled Oscillator) has to increase, decrease, or be kept constant. The frequency of the internal VCO corresponds to the frequency of the emitted sound signal. In this way a phase difference between the VCO frequency and that of the reception signal is eliminated. Since the PLL circuit can only control in a predefined frequency range (latching range), the latching range has to be selected in such a way that it matches the measuring range.

The phase shift is controlled in step C. For this purpose, the gas concentration sensor can additionally have an amplifier that amplifies the reception signal to a necessary level. A Schmitt trigger connected downstream can subsequently generate the digital square-wave signals necessary for the phase comparator.

In a step F, a temperature of the gas or gas mixture in the measuring range or in the measuring chamber 1 is detected. In step G, the detected temperature is taken into account during the determination of the change in the composition of the gas mixture (step D). In this way, accuracy of the measuring method is improved.

In step E, the transmission of the specific change in the composition of the gas mixture to a control unit of the motor vehicle subsequently takes place. Given 100% air as the reference sound signal and a frequency used of 4.11 kHz, the useful measuring range of the concentration sensor in a scavenging line of the activated carbon filter is, as explained at the beginning, approximately 400 Hz. This means that, in the case of a maximum expected proportion of fuel of 40% in the scavenging air, the frequency is reduced from originally 4.11 kHz to 3.70 kHz.

To simplify the method, the useful measuring range can be divided into three or five ranges, with the result that just one signal, which represents one of the measuring ranges, is transmitted to the control unit. In this way the control unit knows whether a high, medium or low proportion of fuel vapor is present in the scavenging line. A supply of a quantity of fuel to the internal combustion engine can be correspondingly varied on this basis. In particular, the method is carried out after a cold start of the internal combustion engine, with the result that the gas concentration sensor assumes, for example, some of the functions of the lambda sensor.

Thus, while there have shown and described and pointed out fundamental novel features of the invention as applied to a preferred embodiment thereof, it will be understood that various omissions and substitutions and changes in the form and details of the devices illustrated, and in their operation, may be made by those skilled in the art without departing from the spirit of the invention. For example, it is expressly intended that all combinations of those elements and/or method steps which perform substantially the same function in substantially the same way to achieve the same results are within the scope of the invention. Moreover, it should be recognized that structures and/or elements and/or method steps shown and/or described in connection with any disclosed form or embodiment of the invention may be incorporated in any other disclosed or described or suggested form or embodiment as a general matter of design choice. It is the intention, therefore, to be limited only as indicated by the scope of the claims appended hereto.

The invention claimed is:

1. A gas concentration sensor, comprising:
a sound transmitter configured to emit a sound signal;
a sound receiver configured to receive the sound signal emitted by the sound transmitter;
a control device, which comprises a PLL circuit, configured to adjust a phase shift to a predefinable phase shift between the sound signal emitted by the sound transmitter and the sound signal received by the sound receiver;
a phase comparator, with the PLL circuit configured to adjust a frequency of the emitted sound signal with respect to the received signal; and
an evaluation unit configured to determine a change in a composition of a gas mixture based at least in part on a change in frequency of the sound signal relative to a frequency of a reference sound signal; and
wherein the phase comparator compares the emitted sound signal and the received sound signal to determine whether the frequency of the emitted sound signal has to increase, decrease, or remain constant for the phase shift to correspond to the predefinable phase shift,
wherein the evaluation unit is further configured to divide a maximum measuring range of the sensor into one of 3 regions and 5 regions, and output a signal that corresponds to a respective region as an indication of a change in the composition of the gas mixture.

2. The gas concentration sensor as claimed in claim 1, wherein the sound signal is in an audible sound range up to an ultrasonic range.

3. The gas concentration sensor as claimed in claim 1, wherein at least one of the sound transmitter and the sound receiver is one of a piezo-transducer and a dynamic transducer.

4. The gas concentration sensor as claimed in claim 1, further comprising a measuring chamber having an interior with sound-absorbing surfaces.

5. The gas concentration sensor as claimed in claim 1, wherein the predefinable phase shift is 0°.

6. The gas concentration sensor as claimed in claim 1, wherein the frequency of the reference sound signal is set at 100% air.

7. The gas concentration sensor as claimed in claim 1, wherein the control device maintains the predefinable phase shift during operation of the gas concentration sensor.

8. A motor vehicle having a gas concentration sensor as claimed in claims 1, wherein the gas concentration sensor is arranged on a line of the motor vehicle.

9. The motor vehicle as claimed in claim 8, wherein the gas concentration sensor is arranged between a filter device for filtering fuel vapors and an internal combustion engine, the gas concentration sensor being connected to a control unit for the motor vehicle.

10. The motor vehicle as claimed in claim 8, wherein a change in a proportion of fuel vapor in the gas mixture can be determined with the gas concentration sensor.

11. A method for measuring gas concentration using a gas concentration sensor, comprising:
   emitting a sound signal with a sound transmitter;
   receiving the emitted sound signal with a sound receiver;
   adjusting a phase shift between the emitted sound signal and the received sound signal to a predefinable phase shift by a control device comprising a PLL circuit; and
   determining a change in a composition of a gas mixture based on a change in frequency of the sound signal with an evaluation unit;
   adjusting the frequency of the emitted sound signal by a phase comparator to a predefinable phase shift relative to the received emitted sound signal; and
   comparing, by the phase comparator, the emitted sound signal and the received sound signal to determine whether the frequency of the emitted sound signal has to increase, decrease, or remain constant for the phase shift to correspond to the predefinable phase shift,
   wherein a maximum measuring range of the sensor is divided into one of 3 regions and 5 regions, and a signal that corresponds to a respective region is transmitted to a control unit as an indication of a change in the composition of the gas mixture.

12. The method for measuring gas concentration as claimed in claim 11, further comprising:
   transmitting the determined change in the composition of the gas mixture to the control unit of the motor vehicle, wherein the gas concentration sensor is arranged in a motor vehicle between a filter device for filtering fuel vapors and an internal combustion engine.

13. The method for measuring gas concentration as claimed in claim 12, further comprising:
   detecting a temperature; and
   determining the change in the composition of the gas mixture based at least in part on the detected temperature.

14. A method for measuring gas concentration using a gas concentration sensor, comprising:
   emitting a sound signal with a sound transmitter;
   receiving the emitted sound signal with a sound receiver;
   adjusting a phase shift between the emitted sound signal and the received sound signal to a predefinable phase shift by a control device comprising a PLL circuit; and
   determining a change in a composition of a gas mixture based on a change in frequency of the sound signal with an evaluation unit;
   adjusting the frequency of the emitted sound signal by a phase comparator to a predefinable phase shift relative to the received emitted sound signal; and
   comparing, by the phase comparator, the emitted sound signal and the received sound signal to determine whether the frequency of the emitted sound signal has to increase, decrease, or remain constant for the phase shift to correspond to the predefinable phase shift,
   wherein the method is performed in the motor vehicle at a time at which a lambda probe of the motor vehicle is in a non-operationally ready state.

15. The method for measuring gas concentration as claimed in claim 14, wherein the lambda probe of the motor vehicle is in the non-operationally ready state after a cold start of the internal combustion engine of the motor vehicle.

\* \* \* \* \*